United States Patent [19]

Tucker

[11] Patent Number: 4,539,003
[45] Date of Patent: Sep. 3, 1985

[54] ANGIO-CATHETER/INFUSION TUBING LOCK

[76] Inventor: Annabelle D. Tucker, 4480 Sherman Oaks Cir., Sherman Oaks, Calif. 91403

[21] Appl. No.: 435,774

[22] Filed: Jan. 24, 1983

[51] Int. Cl.³ .............................................. A61M 5/00
[52] U.S. Cl. ..................................... 604/93; 604/905; 285/114
[58] Field of Search .................. 604/93, 905; 285/114; D24/54

[56] References Cited

U.S. PATENT DOCUMENTS

| D. 271,904 | 12/1983 | Tucker | D24/54 |
| 3,782,383 | 1/1974 | Thompson et al. | 604/177 |
| 3,881,753 | 5/1975 | Bochory | 285/114 X |
| 4,082,094 | 4/1978 | Dailey | 604/93 |
| 4,230,109 | 10/1980 | Geiss | 604/93 |

FOREIGN PATENT DOCUMENTS 1506163 4/1978 United Kingdom .................. 604/93

Primary Examiner—Dalton L. Truluck

[57] ABSTRACT

A clamp for control of separation of couplers in intravenous feeding and monitoring systems that is open along its vertical length to receive and secure various infusion tubing couplers by embracing raised or soft areas of said couplers with its inner horizontal gripping ridges and grooves to prevent axial and radial movements that may cause leaking or separation of friction or needle insert connections.

7 Claims, 6 Drawing Figures

U.S. Patent  Sep. 3, 1985  4,539,003

ANGIO-CATHETER/INFUSION TUBING LOCK

BACKGROUND OF INVENTION

The present invention relates to a universal safety locking clamp for various infusion system couplings to ensure against accidental separation of said couplings in intravenous feeding or pressure measurement equipment.

The friction connections and needle insert in additive line plugs (including heparin locks) of intravenous feeding systems are vulnerable to separation force by patient activity pulling on connections or by body heat expanding hub of plastic catheter while cool infusion fluid constricts male coupling insert to loosen connection frequently resulting in loss of blood or infusion fluid, soiling of bed clothes, the additional expense of replacing contaminated equipment, loss in nursing time to correct the problem and placing the patient at risk, particularly, if air or contaminates are admitted into a separated central line.

There is a need for a simple, convenient, one-step method of securing the various couplers in intravenous feeding and pressure monitoring equipment that may be applied after connections are made, that is comfortable to wear and apply, unobtrusive and safe for the patient in application and use.

SUMMARY AND OBJECTS OF INVENTION

The primary object of this invention is to provide a safety locking clamp to secure various intravenous feeding system couplers such as angio-catheters, heparin locks, central or additive lines and the main intravenous tubing line to minimize the risk of separation to ensure continuity of procedure.

An additional object of this invention is to provide a lock that is easy and comfortable to apply or remove without a twisting motion and needs no assembly or additional equipment to maintain placement on coupling.

Another object of this invention is to provide a lock that is resilient and can be pulled to expand its vertical opening to receive connected coupler and when released, embrace couplings' raised or soft areas within its inner ridges and grooves to brace against axial and radial movement while avoiding interference with pump on tubing.

A further object of this invention is to provide a safety clamp that conforms to basic shape of coupler and is free of projections that may catch on objects interfering with comfort of patient.

Another object of this invention is to provide a safety clamp that secures coupler when hub of catheter expands from body heat while infusion fluid cools male connector of tubing, loosening coupler connection and allowing seepage of fluid to loosen tape frequently resulting in separation and contamination of coupler.

A further object of this invention is to provide a safety clamp that is versatile and fits the variety of couplers confronted in the various intravenous systems.

To attain these objectives the present invention provides a clamp for restricting the radial and axial movements of intravenous system couplers maintaining a secure connection by embracing raised or soft part on couplers with its inner ridges and grooves, whose resiliant tube-like body may be pulled open wider at its vertical separation to receive coupler after connection is made and retain itself when released on coupler.

THE DRAWINGS

DETAILED DESCRIPTION

Figure 1:
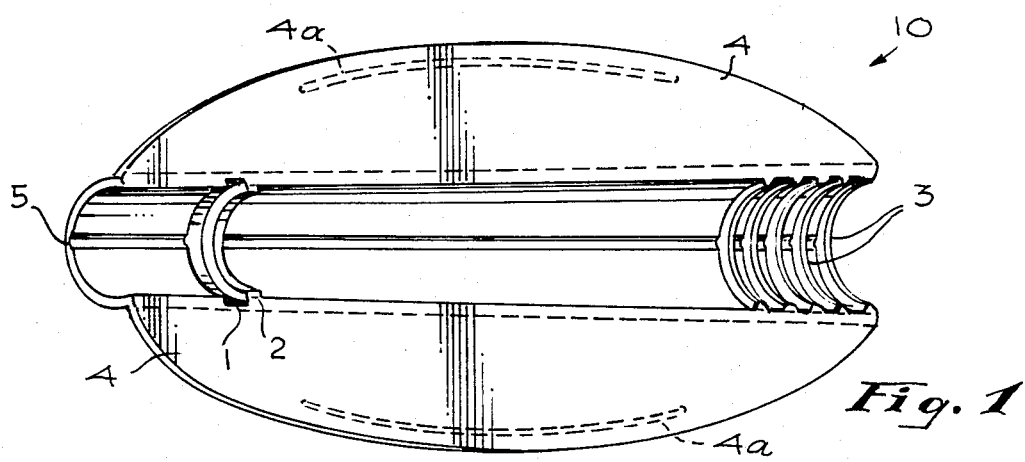
FIG. 1 is a bottom view of clamp showing interior ridges and grooves and the smooth underside of pull wings.

FIG. 1 shows greatly enlarged interior of clamp with groove 1 and ridge 2 at front end of clamp, to fit over raised edge of hub of insertion needle or catheter and ridges 3, at back end, to fit over and grasp raised areas of connector or near edge of rubber pump on intravenous tubing. Flexible, wing-like extensions 4 of base of clamp are for use in extending base opening for easier application or removal of clamp. Also shown is a vertical groove 5 inside arch of tunnel extending from front to back of clamp to allow a flexible line from which to extend base opening. Horizontal groove 1 and ridges 2 and 3 may be bisected along vertical groove 5 to allow more flexibility and complete groove 5.

Figure 2:
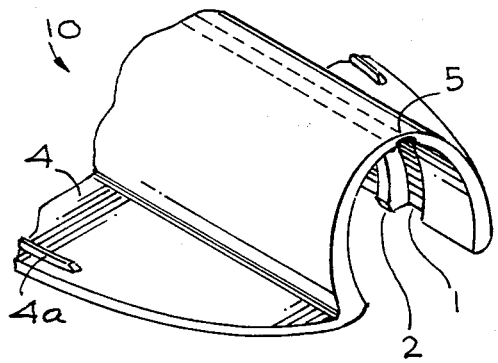
FIG. 2 is a ¾ view of front of clamp showing thinning of wall at top of arch for viewing connector contents if made of transparent plastic material and showing interior groove to grip front item to be braced.

FIG. 2 shows a partial perspective front view of clamp with thinner wall of vertical flexible groove 5 at top interior of tunnel with horizontal groove 1 and ridge 2 at front interior and flexible wing pulls 4 extending out from base of clamp with ridge 4a.

Figure 3:
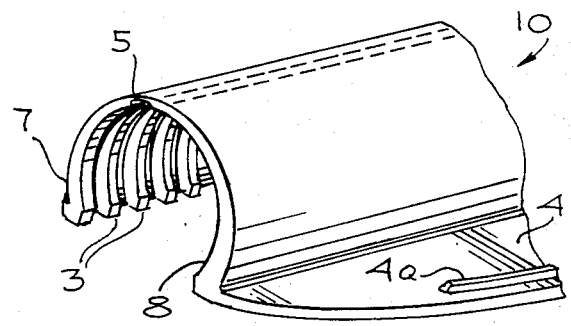
FIG. 3 is a ¾ back view of this invention showing interior ridges.

FIG. 3 shows partial perspective view of clamp with horizontal ridges 3 of interior wall. Side walls 7 are shown thicker at base forming flat interior side walls and curved interior at base 8 to allow firmer grasp on item to be braced. Also shown is the gradual decrease of interior depth of flex groove 5 (front to back) in arch of clamp.

Figure 4:
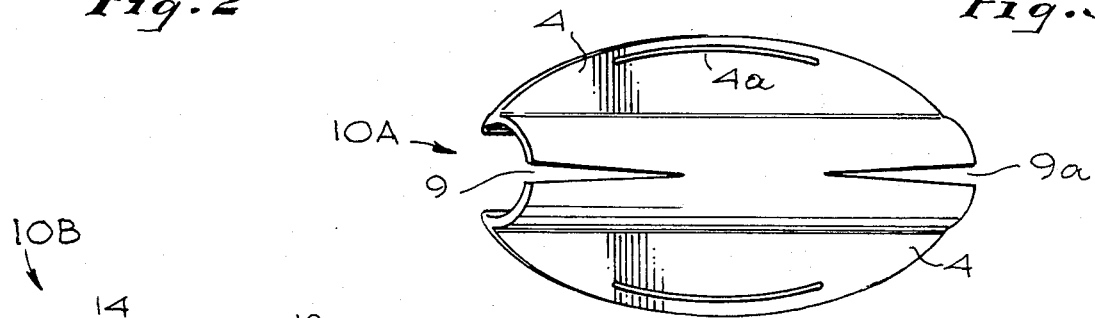
FIG. 4 is a top view of a variation of clamp to provide viewing of connector if opaque plastic material is used in manufacturing.

FIG. 4 is a top view of a variation of the clamp 10A that provides viewing of fluid flow in connector, when in use, through vertical slit 9 in front arch of body of clamp and may provide a slit 9a at opposite end of arch to equalize pressure of clamp. Viewing slit may be necessary if opaque plastic material is used in manufacturing.

Figure 5:
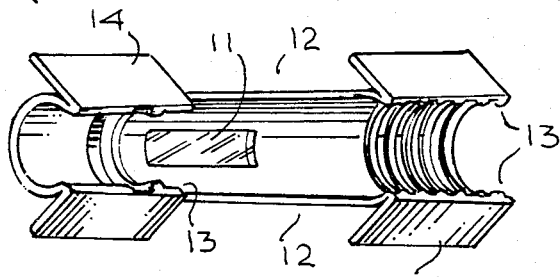
FIG. 5 is a bottom view of a variation of clamp to be used on additive lines and provides viewing through a window cut-out in center front of arch, eliminates central body sides separating wings which are stiff pressure openers for base of clamp.

FIG. 5 is a bottom view of clamp 10B that may be used on additive lines and provides a viewing window 11 cut out (or thinned wall if transparent material) in center front of arch and may eliminate central body sides 12 forming two clamping areas 13 on each side of clamp that extends base opening by pressure placed at top of firm wings 14, rising from base of clamp, against upper body of clamp sides. Otherwise 10B has the same features as 10A.

Figure 6:
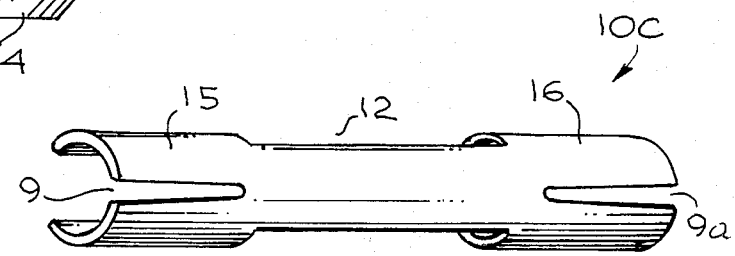
FIG. 6 shows a top view of a variation of FIG. 4 with central body sides eliminated and with opening slits at either end of tunnel arch for viewing and may be used on additive lines as a snap on brace eliminating need for wing pulls.

FIG. 6 shows a top view of a clamp 10C with central body sides 12 eliminated as in FIG. 5 and with viewing slits 9 and 9a at either end of clamp arch with both ends 15 and 16 narrowing diameter to allow flexibility to fit the various size items to be braced in additive medication lines. This variation may be snapped into place with pressure or provide small pull wings along base as shown in 10B-14.

The actual size of a clamp is about 1.5" in length, ¼" at front and ⅜" at rear diameter.

In the foregoing descriptions, specific examples have been used to describe the invention. It is understood by those skilled in the art that certain modifications can be made to these examples without departing from the spirit and scope of the invention.

I claim:

1. A safety locking clamp to secure various size friction couplers in intravenous feeding systems comprising an elongated hollow tubular body formed of resiliant plastic material, said body being provided with an elongated slot extending the entire length of the body, said clamp body having an internal wall structure with ridge means formed internally around the circumference thereof at each end of said body, said clamp further having pull tab means extending laterally from the slot edges whereby said resiliant clamp body may be applied over a coupling by pulling the slot wider and thereafter releasing it over the coupling via said pull tab means, said clamp wall having increased thickness at the junction area of slot edges and pull tab means to provide added gripping strength to said clamp in this area.

2. A locking device as in claim 1 wherein said means of pulling open vertical slot in brace body is assisted by rigid pull tabs provided at either side of vertical slot extending out from opening.

3. A locking device as in claim 1 that provides one or more inner vertical grooves that become outer ridges along entire length of body of brace, serrating inner horizontal ridges and grooves allowing expansion of circumference of brace to fit the various sizes of couplings.

4. A safety locking clamp as described in claim 3 that provides the pull tabs described in claim 2.

5. A flexible safety locking clamp as described in claim 1 that provides an expanding slit at either or both ends of top of body of clamp to allow increase in end circumference of clamp to fit unequal size in various coupling ends.

6. A clamp as described in claims 1, 3 or 5 that provides an inner horizontal groove at one end to embrace raised rim of an angio-catheter and multiple inner horizontal ridges at the other end to grasp the near end of rubber pump on intravenous tubing.

7. A clamp as described in claim 6 that provides pull tabs to open vertical slot wider as described in claim 2.

* * * * *